United States Patent [19]

Voit

[11] 4,308,229
[45] Dec. 29, 1981

[54] STERILIZATION APPARATUS AND METHOD

[76] Inventor: J. Kenneth Voit, 6963 St. Andrews Rd., Columbia, S.C. 29210

[21] Appl. No.: 184,105

[22] Filed: Sep. 4, 1980

[51] Int. Cl.$^3$ .......................... A61L 2/02; A61L 2/04; A61L 2/18
[52] U.S. Cl. ........................................ 422/20; 422/28; 422/116
[58] Field of Search ................ 422/20, 116, 28; 134/1

[56] References Cited

U.S. PATENT DOCUMENTS

| | | | |
|---|---|---|---|
| 3,697,222 | 10/1972 | Sierra | 422/20 |
| 3,708,263 | 1/1973 | Boscher | 422/20 |
| 3,912,450 | 10/1975 | Boscher | 422/20 |
| 4,211,744 | 7/1980 | Boscher | 422/20 |

FOREIGN PATENT DOCUMENTS

| | | | |
|---|---|---|---|
| 947699 | 1/1964 | United Kingdom | 422/20 |
| 947700 | 1/1964 | United Kingdom | 422/20 |

*Primary Examiner*—Barry Richman
*Attorney, Agent, or Firm*—Jones, Thomas & Askew

[57] ABSTRACT

A sterilization apparatus and method according to which articles are sterilized by subjecting them to an ultrasonic/heat activated disinfectant liquid in the presence of heat and ultrasonic vibrations. The preferred disinfectant liquid includes a quaternary ammonium compound and a surfactant at a pH of 12. Treatment according to the invention results in the killing of vegetated bacteria, fungi, viruses and spores.

5 Claims, 3 Drawing Figures

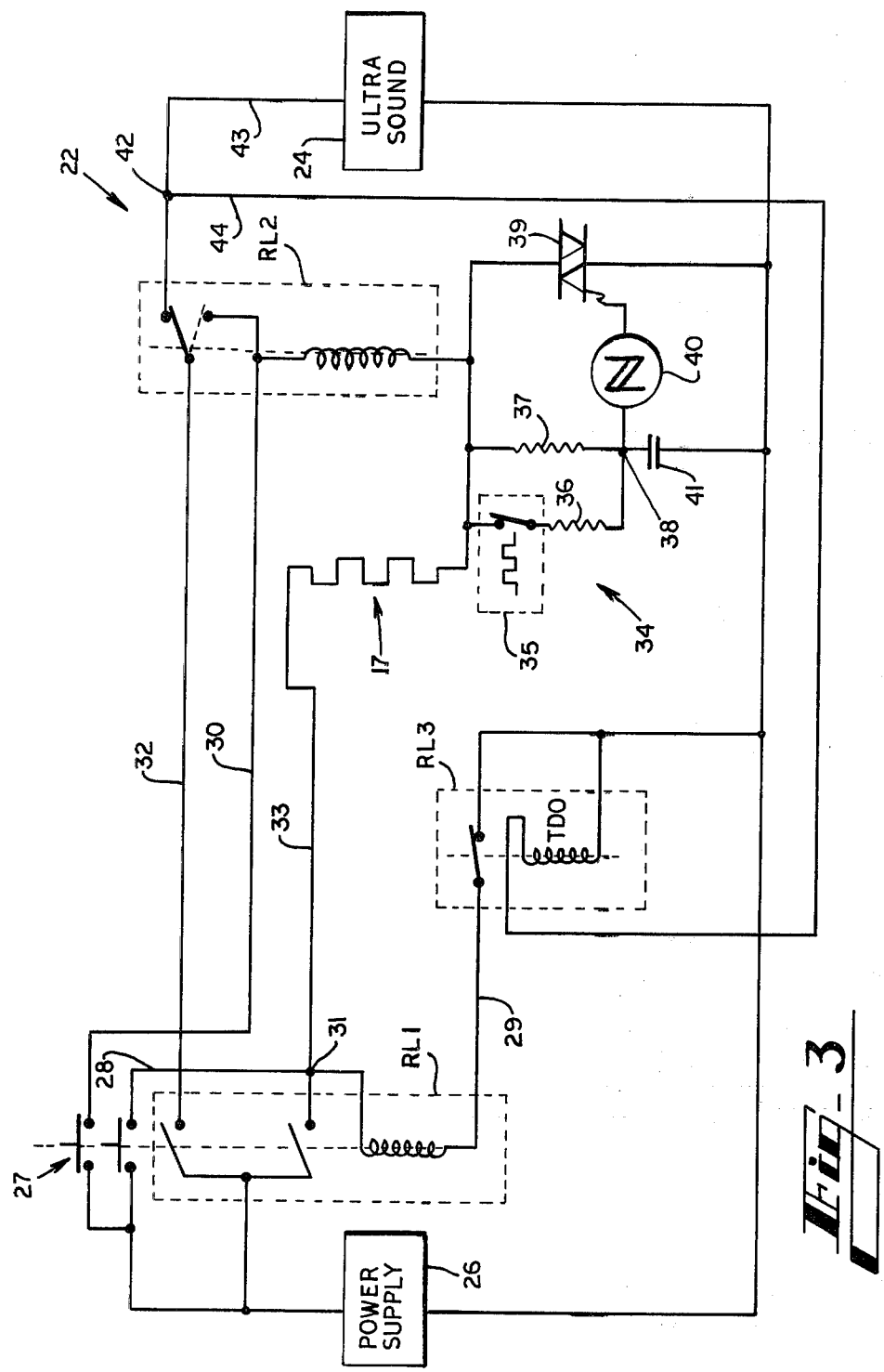

STERILIZATION APPARATUS AND METHOD

TECHNICAL FIELD

The present invention relates to sterilization techniques, and more particularly relates to a method and apparatus for sterilization using a heated, ultrasonic disinfectant bath.

BACKGROUND ART

Sterilization of medical equipment and accessories is of paramount importance in the proper operation of a hospital, clinic, private doctor's office or dentist's office. To effectively sterilize instruments and equipment, highly resistant spores must be killed as well as vegetative bacteria, fungi and virus.

Prior to the present invention, effective sterilization of, for example, surgical instruments has been accomplished in hospitals primarily by either autoclaving or by exposure of the instruments to ethylene oxide. Autoclaving is steam sterilization in which the instruments and other materials to be sterilized are exposed to high temperature and high pressure. Autoclave chambers are expensive to own and to operate. The chambers must be periodically tested with spore strips to assure continuing effectiveness, temperature and pressure must be constantly monitored by the user, and periodic maintenance must be performed. Sterilization by ethylene oxide requires expensive ethylene oxide chambers in which the materials can be exposed to the ethylene oxide in a vacuum for good penetration. Once the materials have been treated with the ethylene oxide, a number of hours must lapse before the materials can be used to allow for evaporation of toxic gases from the materials. In industrial applications, oftentimes ionizing radiation is used as a sterilization method. Each of the typical prior sterilization methods is very expensive, thus tending to restrict their availability to hospitals and other large institutions. Such methods are generally beyond the financial grasp of small firms of private physicians and dentists. Furthermore, typical prior art sterilization methods require a long period of time, generally in excess of eight hours, to complete proper sterilization of the materials. Therefore, a user of the prior sterilization methods must bear the added expense of owning a number of separate sets of instruments and other materials in order that there is one set on hand while the others are being sterilized.

When sterilization by the foregoing methods is impracticable, for financial or other reasons, physicians and dentists can disinfect instruments by use of cold baths of chemical solutions. The majority of the most commonly used known disinfectants, although they are often effective for killing vegetative bacteria and fungi, are incapable of killing spores such as tetanus and hepatitis spores. Many of the most effective disinfectants such as glutaraldehyde, formaldehyde, phenol and chlorine possess undesirable qualities. For example, the disinfectant may be toxic, it may develop noxious fumes, cause skin irritation or allergic reaction. More importantly, glutaraldehydes and phenols have recently been placed on the list of carcinogens as being probable cancer forming agents. Whenever possible, these disinfectants are being removed from the market.

Quaternary ammonium compounds can be used as effective disinfectants against gram positive organisms, especially streptococcus and staphylococcus. Quaternary ammonium compounds are non-toxic, essentially odor free, non-allergenic and otherwise are physiologically safe, but are among the least effective disinfectants when used alone. For example, quaternary ammonium compounds are relatively ineffective against gram negative organisms, and do not effectively kill spores.

SUMMARY OF THE INVENTION

The present invention provides an improved method and apparatus for cleaning and sterilizing materials and solves the need for effectively killing bacteria and spores without the use of the complex and expensive techniques of the prior art. Generally described, the method of the present invention comprises the steps of subjecting materials to be sterilized to the combined effects of ultrasonic vibration, heat and a disinfecting agent of a type that is activated by a combination of ultrasound and heat. In the preferred method of the present invention, the disinfectant used preferably includes a quaternary ammonium compound. The heat applied under the present invention, when utilizing the preferred disinfectant, is preferably approximately 78° C. Complete sterilization, defined as the total kill of spores, bacteria, fungi and virus, is accomplished by the present invention generally in under about twenty minutes.

The sterilization apparatus of the present invention comprises a device for functionally performing the aforementioned method of the present invention. Broadly described, the apparatus comprises a container for receiving articles to be sterilized containing an ultrasonic/heat activated disinfectant liquid, a means for heating the liquid, and a means for propagating ultrasound through the liquid. The apparatus can further comprise a temperature detecting and regulating device for maintaining the temperature of the liquid at a predetermined temperature, a switching device for actuating the ultrasonic vibrator in response to the liquid attaining a predetermined temperature, and a timing device for cutting off the heat and ultrasound after a predetermined length of time.

Therefore, it is an object of the present invention to provide an improved method and apparatus for sterilizing materials.

Another object of the present invention is to provide a sterilizing system for completely sterilizing materials in less than one hour.

Yet another object of the present invention is to provide a sterilizing system which both cleans and sterilizes materials utilizing a disinfectant including a quaternary ammonium compound as a sterilizing agent.

Still another object of the present invention is to provide a sterilizing system in which sterilization is effected by combining the effects of ultrasonic cavitation, heat and a liquid disinfectant.

Another object of the present invention is to provide an inexpensive, portable sterilizing apparatus for use in private offices of physicians and dentists.

Yet another object of the present invention is to provide a sterilizing system which requires little or no human monitoring for successful, complete and safe sterilization of articles.

Other objects, features and advantages of the present invention will become apparent upon reading and understanding the following specification, when taken in conjunction with the accompanying drawing and the appended claims.

BRIEF DESCRIPTION OF THE DRAWING

FIG. 3 is a schematic diagram of a control circuit for operating a sterilization apparatus embodying the present invention.

DETAILED DESCRIPTION

Figure 1:
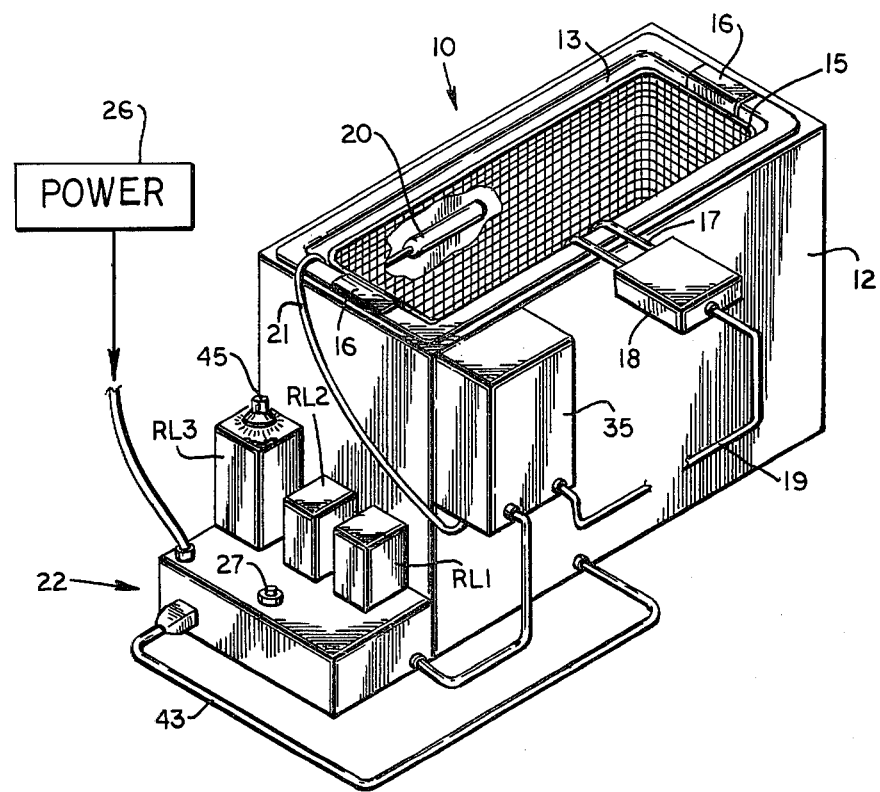
FIG. 1 is a pictorial view of a sterilization apparatus embodying the present invention.

Referring now in more detail to the drawing, in which like numerals represent like parts throughout the several views, FIG. 1 shows a sterilization apparatus 10 embodying the present invention. The sterilization apparatus 10 includes a box-like frame 12 which supports a stainless steel bath receptacle 13. The bath receptacle 13 opens upwardly so as to receive a basket 15 therein. The basket 15 is removable from the bath receptacle 13 so that articles such as surgical tools and instruments can be placed in the basket and lowered into the bath receptacle 13. The basket 15 is shown removed from the bath receptacle 13 and in an inverted position in FIG. 2. The basket 15 includes a pair of lips 16 extending from opposite ends of the basket at the top edge thereof. The lips 16 extend outwardly from the basket a sufficient distance to engage opposite sides of the bath receptacle 13 so that the basket 15, when inserted into the bath receptacle 13, is suspended therein from the lips 16. The basket 15 comprises a mesh material, preferably comprising a metal not subject to deterioration under the conditions within the bath receptacle as described below. The mesh construction of the basket 15 allows a liquid in the receptacle 13 to flow around articles in the basket 15, and allows the propagation of ultra sonic vibrations within such a liquid through the basket 15.

Figure 2:
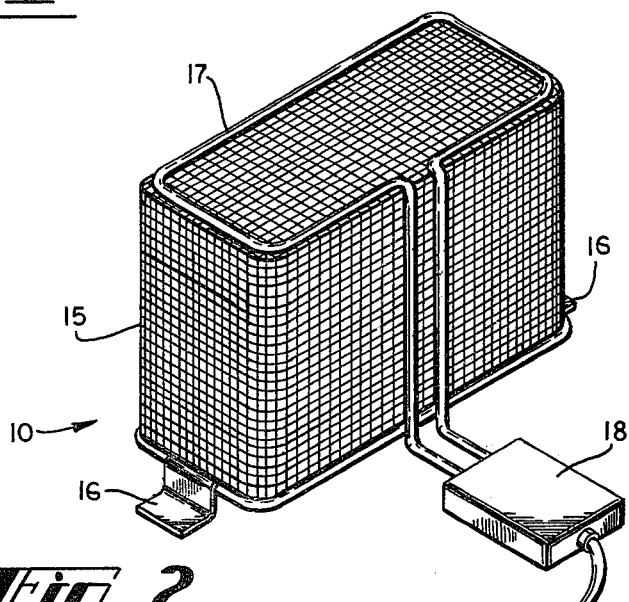
FIG. 2 is a pictorial view of the basket assembly of the apparatus shown in FIG. 1, removed from the liquid receptacle and overturned to expose the configuration of the heating element.

A heating element 17, best shown in FIG. 2, is fixed to the exterior of the basket 15 for heating a liquid within the bath receptacle 13. The heating element 17 is a rod-type element forming a loop around the bottom perimeter of the basket 15, the ends of the loop extending as parallel rods upwardly along one side of the basket 15, as shown in FIG. 2. The two ends of the loop formed by the heating element 17 enter a cable connector box 18 in which they are connected to a cable leading to the power supply and control circuitry that will be described hereinafter.

In FIG. 1, a portion of the basket 15 is broken away to show the location of a temperature sensor or thermostat 20 that is fixed to the side of the bath receptacle 13. The temperature sensor 20 is connected by means of a cable 21 to the control circuitry. Beneath the bath receptacle 13 is an ultrasonic generator (not shown) of a conventional type for generating ultrasonic vibrations in a liquid contained in the bath receptacle 13. The ultrasonic generator is also connected to the control circuitry by a cable 43.

An essential element of the present invention is the selection of an effective disinfectant liquid to be placed in the bath receptacle 13. The disinfectant liquid selected must have the characteristic of being activated by a combination of heat and ultrasound to enable the disinfectant liquid to kill spores as well as vegetative bacteria, fungi and viruses. The preferred disinfectant liquid includes a quaternary ammonium compound, a surfactant, a dehydraization agent and a perfume in a demineralized water base, with the pH of the solution being adjusted to be between 8.5-14. It will be understood by those skilled in the art that quaternary ammonium compounds are safe to use and leave no toxic residual. The preferred quaternary ammonium compound is benzothonium chloride at a concentration of 1:400. Acceptable quaternary ammonium compounds further include, for example, products sold by Rohm & Haas Co. under the trademarks Hyamine 1600, Hyamine 3500 and Hyamine 3509. The preferred surfactant is a polyethoxyethanol commercially available under the tradename "Triton X-100" at a preferred concentration of 1:400. Dimethylsulfoxide can also be used effectively as the surfactant but is subject to government regulation for use around people. The preferred dehydraization agent is isopropanol. The preferred perfume is a 0.2 of 1% proportion of Alpine. The preferred pH is about 12.

A control circuit 22 for the apparatus 10 is shown in a schematic representation in FIG. 3. The ultrasonic generator 24 is shown diagrammatically in FIG. 3, and is connected for operation in a particular sequence with the heating element 17 and a 115 volt AC power supply 26. The high side of the power supply 26 includes a normally opened, double pole, momentary action switch 27. One contact of switch 27 is connected along line 28 to the coil of a relay RL1, and then along line 29, through the normally closed contacts of a time delay relay RL3, and then to the ground side of the power supply 26. The other contact of the switch 27 connects the power supply 26 along a line 30 to the coil of a relay RL2. The momentary connection of the power supply through the switch 27 closes a double set of contacts associated with the relay RL1, connecting the power supply 26 to the coil of the relay RL1 through point 31, thereby latching the relay RL1 so that its contacts remain closed even after the switch 27 is released. The initial surge of power along the line 30 to the coils of the relay RL2 causes the contacts of the relay RL2 to change from the solid line position shown in FIG. 3 to the dotted line position shown in FIG. 3. This connects the power supply to the coils of the relay RL2 so that the contacts stay in the dotted line position after the switch 27 is released.

The operation of the relay RL1 which connected the point 31 to the power supply 26 connects the power supply 26 through the point 31 to the high side of the heating element 17. The low side of the heating element 17 and the coil of the relay RL2 are connected together and are connected to the ground side of the power supply 26 through the main terminals of a triac 39. The firing of the triac 39 is controlled by a full-wave phase control device 34. In the phase control device 34, resistor 37 is connected to the low side of the heating element 17 and to a point 38. An asymetrical silicon bilateral switch 40 is connected from the gate of the triac 39 to the point 38. The use of an asymetrical silicon bilateral switch (ASBS) is well known to eliminate the "snap-on" effect in triggering characteristics of triacs. The point 38 is connected to the ground side of the power supply 26 through a capacitance 41.

The firing of the triac 39 is normally controlled by the charging of the capacitance 41 through the resistance 37. However, the low side of the heating element 17 is connected to the point 38 through a temperature sensitive switch 35 which is responsive to an input signal from the thermostat 20, and through a resistance 36 in series with the switch 35. The resistance 36 is approximately one hundred times smaller than the resistance 37, the preferred values being 4.7 kilohms for the resistance 36, 390 kilohms for the resistance 37 and 0.2 microfarads for capacitance 41. Thus, when the temperature sensed by the thermostat 20 is below a predetermined value, the switch 35 remains closed and the resistance 36 shunts the resistance 37. The low value of the resistance 36 allows the triac to fire through almost the entire AC cycle. This results in a large average voltage across the heating element 17 and rapid heating of the liquid disinfectant in the bath receptacle 13.

When the temperature sensed by the thermostat 20 rises above the predetermined value, the switch 35 opens, eliminating the resistance 36 from the circuit. The resistance 37 is no longer shunted, and the high value of the resistance 37 severely limits the portion of the AC cycle during which the triac 39 fires. This in turn reduces the average voltage across the coil of the relay RL2 to a value that is insufficient to maintain the relay RL2 in an energized condition. Thus, the contacts of the relay RL2 return to their solid line position. Also, the voltage across the heating element 17 continues at a greatly reduced level to maintain the temperature of the liquid disinfectant close to the predetermined value. It will be seen that if the temperature falls below the predetermined value, the switch 35 will again close and the heating element 17 will operate at full power until the temperature is regained and the switch 35 again opens.

The predetermined temperature at which the switch 35 opens should be selected to be within a range from 60°-80° C., preferably 78° C. At lower temperatures sterilization does not occur rapidly enough. At 60° C. the apparatus 10 must be operated for 60-90 minutes. Above 80° C., plastic parts begin to melt and metal instruments are dulled. A hotter liquid also presents a possible hazard to the operator if an accident or mistake should occur.

The inactivation of the relay RL2 and the return of its contacts to the solid line position shown in FIG. 3 connects the line 32 from the power supply 26 to a point 42. The point 42 is connected to the ultrasonic generator 24 through a line 43, and then to the ground side of the power supply 26. Thus, the inactivation of the relay RL2 causes the initiation of generation of ultrasonic vibrations in the liquid disinfectant in the bath receptacle 13. The point 22 is also connected through a line 44 to the high side of the coil of a time delay open relay RL3, the low side of which is connected to the ground side of the power supply 26. The time delay open relay has normally closed contacts and is selected to open its contacts after a time delay of at least approximately fifteen minutes. The preferred time delay, during which the ultrasound generator is operative and the temperature is maintained, is twenty minutes. A period of time less than fifteen minutes requires an unacceptably high temperature in the bath. When the relay times out and opens its contacts, the coil of relay RL1 is deenergized and the power supply 26 is cut off from the lines 32 and 33. This results in shutdown of the circuit by disconnecting power from the heating element 17 and the ultrasonic generator 24. The circuit remains "off" until the momentary switch 27 is again depressed.

It should be noted that once the coil of the relay RL2 has been denergized by the opening of the temperature sensitive switch 35, the relay RL2 will not become energized again until the switch 27 is depressed, even if the temperature of the disinfectant liquid falls and causes the switch 35 to close. It should also be understood that the value of the resistance 37 is selected to provide sufficient triggering time of the triac 39 to operate the heating element 17 at a level which will maintain the temperature of the disinfectant liquid near the predetermined desired value. The desired value of temperature of the disinfectant liquid is a range from 60°-80° C., and is preferably 78° C. However, even if the temperature sensitive switch 35 closes during the time period of the relay RL3, the relay RL3 will not be reset, and the circuit will shut down after the normal period of operation of the ultrasonic generator 24 determined by the time delay characteristics of the relay RL3.

Operation of a sterilization apparatus 10 embodying the present invention will be apparent from the foregoing description. An ultrasound/heat activated disinfectant liquid is placed in the bath receptacle 13. The basket 15 is removed from the receptacle 13 and articles to be sterilized are placed therein. The basket is then lowered into the liquid within the receptacle 13 until it is suspended by the lips 16 hanging on the edge of the receptacle 13. The time period of operation can be adjusted by turning an adjustment knob 45 to change the time delay characteristic of the relay RL3.

At this time, the apparatus 10 is ready for activation, and the user depresses momentarily the switch 27, shown as a button in FIG. 1. This results in energization of the heating element 17, which operates at full power as described above until the disinfectant liquid within the receptacle 13 reaches 78° C. When such temperature is reached, the control circuit 22 automatically reduces the output of the heating element 17 to a maintenance level and initiates operation of the ultrasound generator 24. The generator 24 continues to propagate ultrasound through the disinfectant liquid until the selected time period of the rely RL3 expires and the apparatus 10 is shut off automatically.

The combination of an appropriate disinfectant liquid, the high temperature of the disinfectant liquid and the ultrasonic vibrations in the process according to the invention results in thorough cleaning of soil from any articles or instruments being treated, breakdown of the protective capsules of spores, and the killing of such spores, vegetative bacteria, fungi and viruses. Although the physical and chemical mechanisms which kill spores and bacteria during operation of the invention are not fully understood, it is believed that the ultrasound cooperates with the surfactant, the pH and the water in the solution to enhance the breakdown of the spore capsules. This allows the quaternary ammonium compound to attack the interior plasma membrane of the spore. The ultrasound also assists in killing the spore once the membrane has been compromised.

It will thus be seen that an apparatus embodying the present invention enjoys many advantages over prior art sterilization techniques. The present apparatus described above is much less complex than prior art devices, is easier to operate, is more economical to construct, operate and maintain, and does not use dangerous chemicals or radiation.

While this invention has been described in detail with particular reference to preferred embodiments thereof, it will be understood that variations and modifications can be effected within the spirit and scope of the invention as described hereinbefore and as defined in the appended claims.

I claim:

1. A method of sterilizing an article comprising the concurrent steps of:

immersing said article in an ultrasonic/heat activated liquid consisting essentially of a quaternary ammonium compound, a polyethoxyethanol and isopropanol, said liquid having a pH in a range from 8.5 to 14;

heating said liquid to a temperature of 60°–80° C.; and propagating ultrasound through said liquid.

2. The method of claim 1 wherein said quaternary ammonium compound comprises benzothonium chloride at a concentration of 1:400; and wherein the concentration of said polyethoxyethanol is 1:400.

3. The method of claim 1 wherein said step of heating said liquid comprises heating said liquid to a predetermined temperature and then maintaining said liquid at said predetermined temperature for a predetermined period of time.

4. The method of claim 3 wherein said predetermined time period is greater than fifteen minutes.

5. The method of claim 3 wherein said step of propagating ultrasound through said liquid comprises propagating said ultrasound responsive to said liquid reaching said predetermined temperature for the duration of said predetermined time.

* * * * *